United States Patent [19]

Rossy et al.

[11] Patent Number: 4,474,785

[45] Date of Patent: Oct. 2, 1984

[54] 2-ARYL-3,4-DIAZABICYCLO[4.N.O]ALK-2-EN-5-ONES, AND COMPOSITIONS FOR TREATING THERMO-EMBOLIC DISORDERS

[75] Inventors: Phillip A. Rossy; Marco Thyes, both of Ludwigshafen; Albrecht Franke, Wachenheim; Horst Koenig, Ludwigshafen; Josef Gries, Wachenheim; Hans D. Lehmann, Hirschberg; Dieter Lenke, Ludwigshafen, all of Fed. Rep. of Germany

[73] Assignee: BASF Aktiengesellschaft, Fed. Rep. of Germany

[21] Appl. No.: 385,272

[22] Filed: Jun. 4, 1982

[30] Foreign Application Priority Data

Jun. 24, 1981 [DE] Fed. Rep. of Germany ....... 3124699

[51] Int. Cl.³ .................. C07D 403/02; A61K 31/40; A61K 31/47; A61K 31/50
[52] U.S. Cl. ..................................... 424/250; 544/235; 260/239.3 B; 548/486; 546/156
[58] Field of Search ................. 544/235; 260/239.3 B; 424/250

[56] References Cited

U.S. PATENT DOCUMENTS

| | | | |
|---|---|---|---|
| 3,746,712 | 7/1973 | Ross et al. | 544/239 |
| 3,812,256 | 5/1974 | Curran | 424/250 |
| 3,824,271 | 7/1974 | Allen, Jr. et al. | 260/465 D |
| 3,888,901 | 6/1975 | Allen, Jr. et al. | 260/465 R |
| 3,931,176 | 1/1976 | Houlihan | 544/239 |
| 4,070,470 | 1/1978 | Nakagawa et al. | 424/250 X |
| 4,258,185 | 3/1981 | Nakao et al. | 544/238 X |
| 4,271,163 | 6/1981 | Thyes et al. | 424/250 |

FOREIGN PATENT DOCUMENTS

| | | |
|---|---|---|
| 2304977 | 8/1974 | Fed. Rep. of Germany . |
| 2727481 | 1/1979 | Fed. Rep. of Germany . |
| 2854191 | 7/1980 | Fed. Rep. of Germany . |
| 44-2991 | 7/1969 | Japan ................. 544/235 |
| 54-135785 | 10/1979 | Japan ................. 424/250 |

OTHER PUBLICATIONS

Chem. Ber. 99 (1966), pp. 1229–1231.

*Primary Examiner*—Donald G. Daus
*Assistant Examiner*—William A. Teoli, Jr.
*Attorney, Agent, or Firm*—Keil & Weinkauf

[57] ABSTRACT

2-Aryl-3,4-diazabicyclo[4.n.O]alk-2-en-5-ones of the formula I

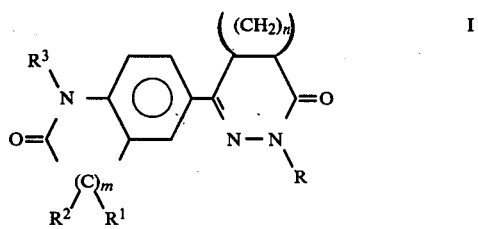

where m and n are identical or different and each is 1, 2 or 3, and R, $R^1$ and $R^2$ are identical or different and each is hydrogen or alkyl of 1 to 6 C atoms, said compounds are useful for treating high blood pressure and thrombo-embolic disorders.

14 Claims, No Drawings

2-ARYL-3,4-DIAZABICYCLO[4.N.O]ALK-2-EN-5-ONES, AND COMPOSITIONS FOR TREATING THROMBO-EMBOLIC DISORDERS

The present invention relates to novel 2-aryl-3,4-diazabicyclo[4.1.0]hept-2-en-5-ones, 2-aryl-3,4-diazabicyclo[4.2.0]oct-2-en-5-ones and 2-aryl-3,4-diazabicyclo[4.3.0]non-2-en-5-ones, a process for their preparation, pharmaceutical formulations containing the compounds, and their use for prophylaxis and therapy of thrombo-embolic disorders and in cases of high blood pressure.

German Laid-Open Application DOS No. 2,854,475 discloses 2-(acylamino)phenyl-3,4-diazabicyclo[4.1.0-]hept-2-en-5-ones for treatment of thrombo-embolic disorders and high blood pressure. U.S. Pat. No. 3,931,176 discloses 2-aryl-3,4-diazabicyclo[4.2.0]oct-2-en-5-ones substituted in the 4-position by hydroxyalkyl. These compounds are stated to have central-depressant properties. Chem. Ber. 99 (1966), 1229 furthermore discloses unsubstituted 2-phenyl-3,4-diazabicyclo[4.2.0]oct-2-en-5-one, but no pharmacological actions are mentioned for this compound.

A number of 6-acylaminophenyl-4,5-dihydro-3(2H)-pyridazinones have been disclosed. For example, German Laid-Open Application DOS No. 1,670,158 discloses 6-(acylamino)phenyl-4,5-dihydro-3(2H)-pyridazinones which are unsubstituted in the 4- and 5-positions and have hypotensive and antiphlogistic properties. German Laid-Open Application DOS No. 2,304,977 discloses 6-phenyl-4,5-dihydro-3(2H)-pyridazinones which carry alkyl in the 4-position and are substituted in the p-position of the phenyl by —$NHR^3$, where $R^3$ is, for example, acyl or ethoxycarbonyl, and which have cardiovascular and antiphlogistic properties. German Laid-Open Application DOS No. 2,150,436 and U.S. Pat. Nos. 3,824,271 and 3,888,901 disclose hypotensive 6-(alkanoylamino)-phenyl-4,5-dihydro-3(2H)-pyridazinones which are substituted in the 5-position by alkyl. German Laid-Open Applications DOS No. 2,727,481 and DOS No. 2,854,191 furthermore disclose 6-(p-alkanoylaminophenyl)-4,5-dihydro-3(2H)-pyridazinones in which the alkanoyl is substituted by one or more halogens and which, because of their platelet aggregation-inhibiting and hypotensive properties, are used as drugs.

German Laid-Open Application DOS No. 2,123,246 discloses hypotensive, coronary vessel-dilating and anti-inflammatory 6-(p-alkanoylaminophenyl)-4,5-dihydro-3(2H)-pyridazinones which carry substituted amino in the alkanoyl. German Laid-Open Application DOS No. 2,157,453 discloses cardiovascular and anti-inflammatory properties for 6-phenyl-4,5-dihydro-3(2H)-pyridazinones which are substituted in the p-position of the phenyl by —$NHCONR^1R^2$, where $R^1$ and $R^2$ are identical or different and each is, for example, hydrogen, alkyl or aryl. Japanese Patent Application No. 53 124-279 furthermore discloses antiallergic, membrane-stabilizing and platelet aggregation-inhibiting 6-p-(alkoxycarbonylaminoalkyl)-phenyl-4,5-dihydro-3(2H)-pyridazinones.

Finally, German Laid-Open Application DOS No. 2,845,220 discloses that 5-(4,5-dihydro-3(2H)-pyridazinon-6-yl)-indolin-2-ones and 6-(4,5-dihydro-3(2H)-pyridazinon-6-yl)-1,2,3,4-tetrahydroquinolin-2-ones inhibit platelet aggregation and lower the blood pressure.

We have found that diazabicyclo[4.n.0]alkenones of the general formula I

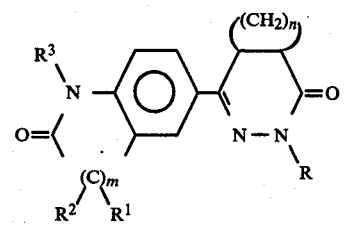

where m and n are identical or different and each is 1, 2 or 3, and R, $R^1$, $R^2$ and $R^3$ are identical or different and each is hydrogen or alkyl of 1 to 6 carbon atoms, have useful pharmacological properties.

The compounds of the formula I according to the invention are prepared by a process wherein a cycloalkanecarboxylic acid of the formula II

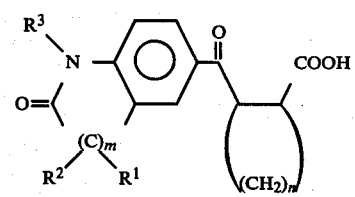

where $R^1$, $R^2$ and $R^3$ have the above meanings, is reacted with a hydrazine of the formula $NH_2NHR$, where R has the above meanings.

Cyclization of a compound of the formula II with a hydrazine of the formula $NH_2NHR$, where R has the above meanings, to give a diazabicyclo[4.n.0]alkenone of the formula I is advantageously carried out in a solvent which is inert under the reaction conditions, in particular a lower alcohol, eg. methanol, ethanol or propanol, a cyclic aliphatic ether, eg. tetrahydrofuran or dioxane, or a dialkylformamide, eg. dimethylformamide, at from 40° to 150° C., preferably from 60° to 120° C. As a rule, from 1 to 1.2 moles of the hydrazine are used per mole of the compound of the formula II.

The starting compounds of the formula II are obtained by reacting a compound of the formula III

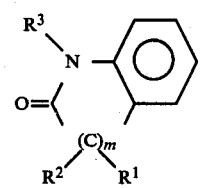

where $R^1$, $R^2$, $R^3$ and m have the above meanings, with cyclopropane-, cyclobutane- or cyclopentane-1,2-dicarboxylic acid anhydride in the presence of aluminum chloride under Friedel-Crafts acylation conditions.

This acylation can be carried out in a solvent, eg. carbon disulfide, at from 25° to 150° C., or in a dimethylformamide/aluminum chloride melt at from 50° to 200° C., preferably from 100° to 160° C. Advantageously, about 10 moles of aluminum chloride and about 2.5 moles of dimethylformamide are used per mole of cyclopropane-, cyclobutane- or cyclopentane-1,2-dicarboxylic acid anhydride, or per mole of a compound of the formula III.

The following compounds according to the invention are obtained, for example, by the above processes: 2-(indolin-2-on-5-yl)-3,4-diazabicyclo[4.3.0]non-2-en-5-one, 2-(1-methylindolin-2-on-5-yl)-3,4-diazabicyclo[4.3.0]non-2-en-5-one, 2-(1-ethylindolin-2-on-5-yl)-3,4-diazabicyclo[4.3.0]non-2-en-5-one, 2-(1-propylindolin-2-on-5-yl)-3,4-diazabicyclo[4.3.0]non-2-en-5-one, 2-(3-methylindolin-2-on-5-yl)-3,4-diazabicyclo[4.3.0]non-2-en-5-one, 2-(3,3-dimethylindolin-2-on-5-yl)-3,4-diazabicyclo[4.3.0]non-2-en-5-one, 2-(3-ethylindolin-2-on-5-yl)-3,4-diazabicyclo[4.3.0]non-2-en-5-one, 2-(3,3-dimethylindolin-2-on-5-yl)-3,4-diazabicyclo[4.3.0]non-2-en-5-one, 2-(3-ethyl-3-methylindolin-2-on-5-yl)-3,4-diazabicyclo[4.3.0]non-2-en-5-one, 2-(1,3-dimethylindolin-2-on-5-yl)-3,4-diazabicyclo[4.3.0]non-2-en-5-one, 2-(1,3,3-trimethylindolin-2-on-5-yl)-3,4-diazabicyclo[4.3.0]non-2-en-5-one, 2-(indolin-2-on-5-yl)-4-methyl-3,4-diazabicyclo[4.3.0]non-2-en-5-one, 2-(indolin-2-on-5-yl)-3,4-diazabicyclo[4.2.0]oct-2-en-5-one, 2-(1-methylindolin-2-on-5-yl)-3,4-diazabicyclo[4.2.0]oct-2-en-5-one, 2-(1-ethylindolin-2-on-5-yl)-3,4-diazabicyclo[4.2.0]oct-2-en-5-one, 2-(1-propylindolin-2-on-5-yl)-3,4-diazabicyclo[4.2.0]oct-2-en-5-one, 2-(3-methylindolin-2-on-5-yl)-3,4-diazabicyclo[4.2.0]oct-2-en-5-one, 2-(3,3-dimethylindolin-2-on-5-yl)-3,4-diazabicyclo[4.2.0]oct-2-en-5-one, 2-(3-ethylindolin-2-on-5-yl)-3,4-diazabicyclo[4.2.0]oct-2-en-5-one, 2-(3,3-diethylindolin-2-on-5-yl)-3,4-diazabicyclo[4.2.0]oct-2-en-5-one, 2-(3-ethyl-3-methylindolin-2-on-5-yl)-3,4-diazabicyclo[4.2.0]oct-2-en-5-one, 2-(1,3-dimethylindolin-2-on-5-yl)-3,4-diazabicyclo[4.2.0]oct-2-en-5-one, 2-(1,3,3-trimethylindolin-2-on-5-yl)-3,4-diazabicyclo[4.2.0]oct-2-en-5-one, 2-(indolin-2-on-5-yl)-4-methyl-3,4-diazabicyclo[4.2.0]oct-2-en-5-one, 2-(indolin-2-on-5-yl)-3,4-diazabicyclo[4.1.0]hept-2-en-5-one, 2-(1-methylindolin-2-on-5-yl)-3,4-diazabicyclo[4.1.0]hept-2-en-5-one, 2-(1-ethylindolin-2-on-5-yl)-3,4-diazabicyclo[4.1.0]hept-2-en-5-one, 2-(1-propylindolin-2-on-5-yl)-3,4-diazabicyclo[4.1.0]hept-2-en-5-one, 2-(3-methylindolin-2-on-5-yl)-3,4-diazabicyclo[4.1.0]hept-2-en-5-one, 2-(3,3-dimethylindolin-2-on-5-yl)-3,4-diazabicyclo[4.1.0]hept-2-en-5-one, 2-(3-ethylindolin-2-on-5-yl)-3,4-diazabicyclo[4.1.0]hept-2-en-5-one, 2-(3,3-diethylindolin-2-on-5-yl)-3,4-diazabicyclo[4.1.0]hept-2-en-5-one, 2-(3-ethyl-3-methylindolin-2-on-5-yl)-3,4-diazabicyclo[4.1.0]hept-2-en-5-one, 2-(1,3-dimethylindolin-2-on-5-yl)-3,4-diazabicyclo[4.1.0]hept-2-en-5-one, 2-(1,3,3-trimethylindolin-2-on-5-yl)-3,4-diazabicyclo[4.1.0]hept-2-en-5-one, 2-(indolin-2-on-5-yl)-4-methyl-3,4-diazabicyclo[4.1.0]hept-2-en-5-one, 2-(1-methyl-indolin-2-on-5-yl)-4-methyl-3,4-diazabicyclo[4.1.0]hept-2-en-5-one, 2-(1,3-dimethylindolin-2-on-5-yl)-4-methyl-3,4-diazabicyclo[4.1.0]hept-2-en-5-one, 2-(1,2,3,4-tetrahydroquinolin-2-on-6-yl)-3,4-diazabicyclo[4.3.0]non-2-en-5-one, 2-(1-methyl-1,2,3,4-tetrahydroquinolin-2-on-6-yl)-3,4-diazabicyclo[4.3.0]non-2-en-5-one, 2-(1-ethyl-1,2,3,4-tetrahydroquinolin-2-on-6-yl)-3,4-diazabicyclo[4.3.0]non-2-en-5-one, 2-(1-propyl-1,2,3,4-tetrahydroquinolin-2-on-6-yl)-3,4-diazabicyclo[4.3.0]non-2-en-5-one, 2-(3-methyl-1,2,3,4-tetrahydroquinolin-2-on-6-yl)-3,4-diazabicyclo[4.3.0]non-2-en-5-one, 2-(3-ethyl-1,2,3,4-tetrahydroquinolin-2-on-6-yl)-3,4-diazabicyclo[4.3.0]non-2-en-5-one, 2-(4-methyl-1,2,3,4-tetrahydroquinolin-2-on-6-yl)-3,4-diazabicyclo[4.3.0]non-2-en-5-one, 2-(4-ethyl-1,2,3,4-tetrahydroquinolin-2-on-6-yl)-3,4-diazabicyclo[4.3.0]non-2-en-5-one, 2-(3,3-dimethyl-1,2,3,4-tetrahydroquinolin-2-on-6-yl)-3,4-diazabicyclo[4.3.0]non-2-en-5-one, 2-(3,3-diethyl-1,2,3,4-tetrahydroquinolin-2-on-6-yl)-3,4-diazabicyclo[4.3.0]non-2-en-5-one, 2-(3,4-dimethyl-1,2,3,4-tetrahydroquinolin-2-on-6-yl)-3,4-diazabicyclo[4.3.0]non-2-en-5-one, 2-(3,4-diethyl-1,2,3,4-tetrahydroquinolin-2-on-6-yl)-3,4-diazabicyclo[4.3.0]non-2-en-5-one, 2-(3-ethyl-4-methyl-1,2,3,4-tetrahydroquinolin-2-on-6-yl)-3,4-diazabicyclo[4.3.0]non-2-en-5-one, 2-(4-ethyl-3-methyl-1,2,3,4-tetrahydroquinolin-2-on-6-yl)-3,4-diazabicyclo[4.3.0]non-2-en-5-one, 2-(3,3,4,4-tetramethyl-1,2,3,4-tetrahydroquinolin-2-on-6-yl)-3,4-diazabicyclo[4.3.0]non-2-en-5-one, 2-(3,4-diethyl-3,4-dimethyl-1,2,3,4-tetrahydroquinolin-2-on-6-yl)-3,4-diazabicyclo[4.3.0]non-2-en-5-one. 2-(1,3-dimethyl-1,2,3,4-tetrahydroquinolin-2-on-6-yl)-3,4-diazabicyclo[4.3.0]non-2-en-5-one, 2-(1,3,4-trimethyl-1,2,3,4-tetrahydroquinolin-2-on-6-yl)-3,4-diazabicyclo[4.3.0]non-2-en-5-one, 2-(1,3,3-trimethyl-1,2,3,4-tetrahydroquinolin-2-on-6-yl)-3,4-diazabicyclo[4.3.0]non-2-en-5-one, 2-(1,4,4-trimethyl-1,2,3,4-tetrahydroquinolin-2-on-6-yl)-3,4-diazabicyclo[4.3.0]non-2-en-5-one, 2-(1,2,3,4-tetrahydroquinolin-2-on-6-yl)-4-methyl-3,4-diazabicyclo[4.3.0]non-2-en-5-one, 2-(1-methyl-1,2,3,4-tetrahydroquinolin-2-on-6-yl)-4-methyl-3,4-diazabicyclo[4.3.0]non-2-en-5-one, 2-(1,3-dimethyl-1,2,3,4-tetrahydroquinolin-2-on-6-yl)-4-methyl-3,4-diazabicyclo[4.3.0]non-2-en-5-one, 2-(1,3,4-trimethyl-1,2,3,4-tetrahydroquinolin-2-on-6-yl)-4-methyl-3,4-diazabicyclo[4.3.0]non-2-en-5-one, 2-(1,2,3,4-tetrahydroquinolin-2-on-6-yl)-3,4-diazabicyclo[4.2.0]oct-2-en-5-one, 2-(1-methyl-1,2,3,4-tetrahydroquinolin-2-on-6yl)-3,4-diazabicyclo[4.2.0]oct-2-en-5-one, 1-(1-ethyl-1,2,3,4-tetrahydroquinolin-2-on-6-yl)-3,4-diazabicyclo[4.2.0]oct-2-en-5-one, 2-(1-propyl-1,2,3,4-tetrahydroquinolin-2-on-6-yl)-3,4-diazabicyclo[4.2.0]oct-2-en-5-one, 2-(3-methyl-1,2,3,4-tetrahydroquinolin-2-on-6-yl)-3,4-diazabicyclo[4.2.0]oct-2-en-5-one, 2-(3-ethyl-1,2,3,4-tetrahydroquinolin-2-on-6-yl)-3,4-diazabicyclo[4.2.0]oct-2-en-5-one, 2-(4-methyl-1,2,3,4-tetrahydroquinolin-2-on-6-yl)-3,4-diazabicyclo[4.2.0]oct-2-en-5-one, 2-(4-ethyl-1,2,3,4-tetrahydroquinolin-2-on-6-yl)-3,4-diazabicyclo[4.2.0]oct-2-en-5-one, 2-(3,3-dimethyl-1,2,3,4-tetrahydroquinolin-2-on-6-yl)-3,4-diazabicyclo[4.2.0]oct-2-en-5-one, 2-(3,3-diethyl-1,2,3,4-tetrahydroquinolin-2-on-6-yl)-3,4-diazabicyclo[4.2.0]oct-2-en-5-one, 2-(3,4-dimethyl-1,2,3,4-tetrahydroquinolin-2-on-6-yl)-3,4-diazabicyclo[4.2.0]oct-2-en-5-one, 2-(3,4-diethyl-1,2,3,4-tetrahydroquinolin-2-on-6-yl)-3,4-diazabicyclo[4.2.0]oct-2-en-5-one, 2-(3-ethyl-4-methyl-1,2,3,4-tetrahydroquinolin-2-on-6-yl)-3,4-diazabicyclo[4.2.0]oct-2-en-5-one, 2-(4-ethyl-3-methyl-1,2,3,4-tetrahydroquinolin-2-on-6-yl)-3,4-diazabicyclo[4.2.0]oct-2-en-5-one, 2-(3,3,4,4-tetramethyl-1,2,3,4-tetrahydroquinolin-2-on-6-yl)-3,4-diazabicylo[4.2.0]oct-2-en-5one, 2-(3,4-diethyl-3,4-dimethyl-1,2,3,4-tetrahydroquinolin-2-on-6-yl)-3,4-diazabicyclo[4.2.0]oct-2-en-5-one, 2-(1,3-dimethyl-1,2,3,4-tetrahydroquinolin-2-on-6-yl)-3,4-diazabicyclo[4.2.0]oct-2-en-5-one, 2-(1,3,4-trimethyl-1,2,3,4-tetrahydroquinolin-2-on-6-yl)-3,4-diazabicyclo[4.2.0]oct-2-en-5-one, 2-(1,3,3-trimethyl-1,2,3,4-tetrahydroquinolin-2-on-6-yl)-3,4-diazabicyclo[4.2.0]oct-2-en-5-one, 2-(1,4,4-trimethyl-1,2,3,4-tetrahydroquinolin-2-on-6-yl)-3,4-diazabicyclo[4.2.0]oct-2-en-5-one, 2-(1,2,3,4-tetrahydroquinolin-2-on-6-yl)-4-methyl-3,4-diazabicyclo[4.2.0]oct-2-en-5-one, 2-(1-methyl-1,2,3,4-tetrahydroquinolin-2-on-6-yl)-4-methyl-3,4-diazabicyclo[4.2.0]oct-2-en-5-one, 2-(1,3-dimethyl-1,2,3,4-tetrahydroquinolin-2-on-6-yl)-4-methyl-3,4-diazabicyclo[4.2.0]oct-2-en-5-one, 2-(1,3,4-trimethyl-1,2,3,4-tetrahydroquinolin-2-on-6-yl)-4-methyl-3,4-diazabicyclo[4.2.0]oct-2-en-5-one, 2-(1,2,3,4-tetrahydroquinolin-2-on-6-yl)-3,4-diazabicyclo[4.1.0]hept-2-en-5-one, 2-(1-methyl-1,2,3,4-tetrahydroquinolin-2-on-6-yl)-3,4-diazabicyclo[4.1.0]hept-2-en-5-one, 2-(1-ethyl-1,2,3,4-tetrahydroquinolin-2-on-6-yl)-3,4-diazabicyclo[4.1.0]hept-2-en-5-one, 2-(1-propyl-1,2,3,4-tetrahydroquinolin-2-on-6-yl)-3,4-diazabicyclo[4.1.0]hept-2-en-5-one, 2-(3-methyl-1,2,3,4-tetrahydroquinolin-2-on-6yl)-3,4-diazabicyclo[4.1.0]hept-2-en-5-one, 2-(3-ethyl-1,2,3,4-tetrahydroquinolin-2-on-6-yl)-3,4-diazabicyclo[4.1.0]hept-2-en-5-one, 2-(4-methyl-1,2,3,4-tetrahydroquinolin-2-on-6-yl)-3,4-diazabicyclo[4.1.0]hept-2-en-5-one, 2-(4-ethyl-1,2,3,4-tetrahydroquinolin-2-on-6-yl)-3,4-diazabicyclo[4.1.0]hept-2-en-5-one, 2-(3,3-dimethyl-1,2,3,4-tetrahydroquinolin-2-on-6-yl)-3,4-diazabicyclo[4.1.0]hept-2-en-5-one, 2-(3,3-diethyl-1,2,3,4-tetrahydroquinolin-2-on-6-yl)-3,4-diazabicyclo[4.1.0]hept-2-en-5-one, 2-(3,4-dimethyl-1,2,3,4-tetrahydroquinolin-2-on-6-yl)-3,4-diazabicyclo[4.1.0]hept-2-en-5-one, 2-(3,4-diethyl-1,2,3,4-tetrahydroquinolin-2-on-6-yl)-3,4-diazabicyclo[4.1.0]hept-2-en-5-one, 2-(3-ethyl-4-methyl-1,2,3,4-tetrahydroquinolin-2-on-6-yl)-3,4-diazabicyclo[4.1.0]hept-2-en-5-one, 2-(4-ethyl-3-methyl-1,2,3,4-tetrahydroquinolin-2-on-6-yl)-3,4-diazabicyclo[4.1.0]hept-2-en-5-one, 2-(3,3,4,4-tetramethyl-1,2,3,4-tetrahydroquinolin-2-on-6-yl)-3,4-diazabicyclo[4.1.0]hept-2-en-5-one, 2-(3,4-diethyl-3,4-dimethyl-1,2,3,4-tetrahydroquinolin-2-on-b 6-yl)-3,4-diazabicyclo[4.1.0]hept-2-en-5-one, 2-(1,3-dimethyl-1,2,3,4-tetrahydroquinolin-2-on-6-yl)-3,4-diazabicyclo[4.1.0]hept-2-en-5-one, 2-(1,4-dimethyl-1,2,3,4-tetrahydroquinolin-2-on-6-yl)-3,4-diazabicyclo[4.1.0]hept-2-en-5-one, 2-(1,3,4-trimethyl-1,2,3,4-tetrahydroquinolin-2-on-6-yl)-3,4-diazabicyclo[4.1.0]hept-2-en-5-one, 2-(1,3,3-trimethyl-1,2,3,4-tetrahydroquinolin-2-on-6-yl)-3,4-diazabicyclo[4.1.0]hept-2-en-5-one, 2-(1,4,4-trimethyl-1,2,3,4-tetrahydroquinolin-2-on-6-yl)-3,4-diazabicyclo[4.1.0]hept-2-en-5-one, 2-(1,2,3,4-tetrahydroquinolin-2-on-6-yl)-4-methyl-3,4-diazabicyclo[4.1.0]hept-2-en-5-one, 2-(1-methyl-1,2,3,4-tetrahydroquinolin-2-on-6-yl)-4-methyl-3,4-diazabicyclo[4.1.0]hept-2-en-5-one, 2-(1,3-dimethyl-1,2,3,4-tetrahydroquinolin-2-on-6-yl)-4-methyl-3,4-diazabicyclo[4.1.0]hept-2-en-5-one, 2-(1,3,4-trimethyl-1,2,3,4-tetrahydroquinolin-2-on-6-yl)-4-methyl-3,4-diazabicyclo[4.1.0]hept-2-en-5-one, 2-(1,3,3-trimethyl-1,2,3,4-tetrahydroquinolin-2-on-6-yl)-4-methyl-3,4-diazabicyclo[4.1.0]hept-2-en-5-one, 2-(1,4-dimethyl-1,2,3,4-tetrahydroquinolin-2-on-6-yl)-4-methyl-3,4-diazabicyclo[4.1.0]hept-2-en-6-one, 2-(2,3,4,5-tetrahydro-benzo[b]azepin-2-(1H)-on-7-yl)-3,4-diazabicyclo[4.3.0]non-2-en-5-one, 2-(1-methyl-2,3,4,5-tetrahydro-benzo[b]azepin-2-(1H)-on-7-yl)-3,4-diazabicyclo[4.3.0]non-2-en-5-one, 2-(3-methyl-2,3,4,5-tetrahydro-benzo[b]azepin-2-(1H)-on-7-yl)-3,4-diazabicyclo[4.3.0]non-2-en-5-one, 2-(4-methyl-2,3,4,5,-tetrahydro-benzo[b]azepin-2-(1H)-on-7-yl)-3,4-diazabicyclo[4.3.0]non-2-en-5-one, 2-(5-methyl-2,3,4,5-tetrahydro-benzo[b]azepin-2-(1H)-on-7-yl)-3,4-diazabicyclo[4.3.0]non-2-en-5-one, 2-(3,4-dimethyl-2,3,4,5,-tetrahydro-benzo[b]azepin-2-(1H)-on-7-yl)-3,4-diazabicyclo[4.3.0]non-2-en-5-one, 2-(3,5-dimethyl-2,3,4,5,-tetrahydro-benzo[b]azepin-2-(1H)-on-7-yl)-3,4-diazabicyclo[4.3.0]non-2-en-5-one, 2-(4,5-dimethyl-2,3,4,5-tetrahydro-benzo[b]azepin-2-(1H)-on-7-yl)-3,4-diazabicyclo[4.3.0]non-2-en-5-one, 2-(1,3-dimethyl-2,3,4,5-tetrahydro-benzo[b]azepin-2-(1H)-on-7yl)-3,4-diazabicyclo[4.3.0]non-2-en-5-one, 2-(1,4-dimethyl-2,3,4,5-tetrahydro-benzo[b]azepin-2-(1H)-on-7-yl)-3,4-diazabicyclo[4.3.0]non-2-en-5-one, 2-(1,5-dimethyl-2,3,4,5-tetrahydro-benzo[b]azepin-2-(1H)-on-7-yl)-3,4-diazabicyclo[4.3.0]non-2-en-5-one, 2-(1,3,4-trimethyl-2,3,4,5-tetrahydro-benzo[]azepin-2-(1H)-on-7-yl)-3,4-diazabicyclo[4.3.0]non-2-en-5-one, 2-(1,3,5-trimethyl-2,3,4,5-tetrahydro-benzo[b]azepin-2-(1H)-on-7-yl)-3,4-diazabicyclo[4.3.0]non-2-en-5-one, 2-(1,4,5-trimethyl-2,3,4,5-tetrahydro-benzo[b]azepin-2-(1H)-on-7-yl)-3,4-diazabicyclo[4.3.0]non-2-en-5-one, 2-(3,4,5-trimethyl-2,3,4,5-tetrahydro-benzo[b]azepin-2-(1H)-on-7yl)-3,4-diazabicyclo[4.3.0]non-2-en-5-one, 2-(1,3,4,5-tetramethyl-2,3,4,5-tetrahydro-benzo[b]azepin-2-(1H)-on-7-yl)-3,4-diazabicyclo[4.3.0]non-2-en-5-one, 2-(2,3,4,5-tetrahydro-benzo[b]azepin-2-(1H)-on-7-yl)-4-methyl-3,4-diazabicyclo[4.3.0]non-2-en-5-one, 2-(1-methyl-2,3,4,5-tetrahydro-benzo[b]azepin-2-(1H)-on-7-yl)-4-methyl-3,4-diazabicyclo[4.3.0]non-2-en-5-one, 2-(1,3-dimethyl-2,3,4,5-tetrahydro-benzo[b]azepin-2-(1H)-on-7-yl)-4-methyl-3,4-diazabicyclo[4.3.0]non-2-en-5-one, 2-(1,4-dimethyl-2,3,4,5-tetrahydro-benzo[b]azepin-2-(1H)-on-7-yl)-4-methyl-3,4-diazabicyclo[4.3.0]non-2-en-5-one, 2-(2,3,4,5-tetrahydro-benzo[b]azepin-2-(1H)-on-7-yl)-3,4-diazabicyclo[4.3.0]oct-2-en-5-one, 2-(1-methyl-2,3,4,5-tetrahydro-benzo[b]azepin-2-(1H)-on-7-yl)-3,4-diazabicyclo[4.2.0]oct-2-en-5 -one, 2-(3-methyl-2,3,4,5-tetrahydro-benzo[b]azepin-2-(1H)-on-7-yl)-3,4-diazabicyclo[4.2.0]oct-2-en-5-one, 2-(4-methyl-2,3,4,5-tetrahydro-benzo[b]-azepin-2-(1H)-on-7-yl)-3,4-diazabicyclo[4.3.0]oct-2-en-5-one, 2-(5-methyl-2,3,4,5-tetrahydro-benzo[b]azepin-2-(1H)-on-7-yl)-3,4-diazabicyclo[4.2.0]oct-2-en-5-one, 2-(3,4-dimethyl-2,3,4,5-tetrahydro-benzo[b]azepin-2-(1H)-on-7-yl)-3,4-diazabicyclo[4.2.0]oct-2-en-5-one, 2-(3,5-dimethyl-2,3,4,5-tetrahydro-benzo[b]azepin-2-(1H)-on-7-yl)-3,4-diazabicyclo[4.2.0]oct-2-en-5-one, 2-(4,5-dimethyl-2,3,4,5-tetrahydro-benzo[b]azepin-2-(1H)-on-7-yl)-3,4-diazabicyclo[4.2.0]oct-2-en-5-one, 2-(1,3-dimethyl-2,3,4,5-tetrahydro-benzo[b]azepin-2-(1H)-on-7-yl)-3,4-diazabicyclo[4.2.0]oct-2-en-5-one, 2-(1,4-dimethyl-2,3,4,5-tetrahydro-benzo[b]azepin-2-(1H)-on-7-yl)-3,4-diazabicyclo[4.2.0]oct -2-en-5-one, 2-(1,5-dimethyl-2,3,4,5-tetrahydro-benzo[b]azepin-2-(1H)-on-7-yl)-3,4-diazabicyclo[4.2.0]oct-2-en-5-one, 2-(1,3,4-trimethyl-2,3,4,5-tetrahydro-benzo[b]azepin-2-(1H)-on-7-yl)-3,4-diazabicyclo[4.2.0]oct-2-en-5-one, 2-(1,3,5-trimethyl-2,3,4,5-tetrahydro-benzo[b]azepin-2-(1H)-on-7-yl)-3,4-diazabicyclo[4.2.0]oct-2-en-5-one, 2-(1,4,5-trimethyl-2,3,4,5-tetrahydro-benzo[b]azepin-2-(1H)-on-7-yl)-3,4-diazabicyclo[4.2.0]oct-2-en-5-one, 2-(3,4,5-trimethyl-2,3,4,5-tetrahydro-benzo[b]azepin-2-(1H)-on-7-yl)-3,4-diazabicyclo[4.2.0]oct-2-en-5-one, 2-(1,3,4,5-tetramethyl-2,3,4,5-tetrahydro-benzo[b]azepin-2-(1H)-on-7-yl)-3,4-diazabicyclo[4.2.0]oct-2-en-5-one, 2-(2,3,4,5-tetrahydro-benzo[b]azepin-2-(1H)-on-7-yl)-4-methyl-3,4-diazabicyclo[4.2.0]oct-2-en-5-one, 2-(1-methyl-2,3,4,5-tetrahydro-benzo[b]azepin-2-(1H)-on-7-yl)-4-methyl-3,4-diazabicyclo[4.2.0]oct-2-en-5-one, 2-(1,3-dimethyl-2,3,4,5-tetrahydro-benzo[b]azepin-2-(1H)-on-7-yl)-4-methyl-3,4-diazabicyclo[4.2.0]oct-2-en-5-one, 2-(1,4-dimethyl-2,3,4,5-tetrahydro-benzo[b]azepin-2-(1H)-on-7-yl)-4-methyl-3,4-diazabicyclo[4.2.0]oct-2-en-5-one, 2-(2,3,4,5-tetrahydro-benzo[b]azepin-2-(1H)-on-7-yl)-3,4-diazabicyclo[4.2.0]hept-2-en-5-one, 2-(1-methyl-2,3,4,5-tetrahydro-benzo[b]azepin-2-(1H)-on-7-yl)-3,4-diazabicyclo[4.1.0]hept-2-en-5-one, 2-(3-methyl-2,3,4,5-tetrahydro-benzo[b]azepin-2-(1H)-on-7-yl)-3,4-diazabicyclo[4.1.0]hept-2-en-5-one, 2-(4-methyl-2,3,4,5-tetrahydro-benzo[b]azepin-2-(1H)-on-7-yl)-3,4-diazabicyclo[4.1.0]hept-2-en-5-one, 2-(5-methyl-2,3,4,5- tetrahydro-benzo[b]azepin-2-(1H)-on-7-yl)-3,4-diazabicyclo[4.1.0]hept-2-en-5-one, 2-(3,4-dimethyl-2,3,4,5-tetrahydro-benzo[b]azepin-2-(1H)-on-7-yl)-3,4-diazabicyclo[4.1.0]hept-2-en-5-one, 2-(3,5-dimethyl-2,3,4,5-tetrahydro-benzo[b]azepin-2-(1H)-on-7-yl)-3,4-diazabicyclo[4.1.0]hept-2-en-5-one, 2-(4,5-dimethyl-2,3,4,5-tetrahydro-benzo[b]azepin-b 2-(1H)-on-7-yl)-3,4-diazabicyclo[4.1.0]hept-2-en-5-one, 2-(1,3-dimethyl-2,3,4,5-tetrahydro-benzo[b]azepin-2-(1H)-on-7-yl)-3,4-diazabicyclo-4.1.0]hept-2-en-5-one, 2-(1,4-dimethyl-2,3,4,5-tetrahydro-benzo[b]azepin-2-(1H)-on-7-yl)-3,4-diazabicyclo[4.1.0]hept-2-en-5-one, 2-(1,5-dimethyl-2,3,4,5-tetrahydro-benzo[b]azepin-2-(1H)-on-7-yl)-3,4-diazabicyclo[4.1.0]hept-2-en-5-one, 2-(1,3,4-trimethyl-2,3,4,5-tetrahydro-benzo[b]azepin-2-(1H)-on-7-yl)-3,4-diazabicyclo[4.1.0]hept-2-en-5-one, 2-(1,3,5-trimethyl-2,3,4,5-tetrahydro-benzo[b]azepin-2-(1H)-on-7-yl)-3,4-diazabicyclo[4.1.0]hept-2-en-5-one, 2-(1,4,5-trimethyl-2,3,4,5-tetrahydro-benzo[b]azepin-2-(1H)-on-7-yl)-3,4-diazabicyclo[4.1.0]hept-2-en-5-one, 2-(3,4,5-trimethyl-2,3,4,5-tetrahydro-benzo[b]azepin-2-(1H)-on-7-yl)-3,4-diazabicylo[4.1.0]hept-2-en-5-one, 2-(1,3,4,5-tetramethyl-2,3,4,5-tetrahydro-benzo[b]azepin-2-(1H)-on-7-yl)-3,4-diazabicyclo[4.1.0]hept-2-en-5-one, 2-(2,3,4,5-tetrahydro-benzo[b]azepin-2-(1H)-on-7-yl)-4-methyl-3,4-diazabicyclo[4.1.0]hept-2-en-5-one, 2-(1-methyl-2,3,4,5-tetrahydro-benzo[b]azepin-2-(1H)-on-7-yl)-4-methyl-3,4-diazabicyclo[4.1.0]hept-2-en-5-one, 2-(1,3-dimethyl-2,3,4,5-tetrahydro-benzo[b]azepin-2-(1H)-on-7-yl)-4-methyl-3,4-diazabicyclo[4.1.0]hept-2-en-5-one and 2-(1,4-dimethyl-2,3,4,5-tetrahydro-benzo[b]azepin-2-(1H)-on-7-yl)-4-methyl-3,4-diazabicyclo[4.1.0]hept-2-en-5-one.

The compounds of the formula I according to the invention have asymmetric carbon atoms in the 1- and 6-positions of the 3,4-diazabicycloalkenone ring and may have asymmetric carbon atoms in the 3-position of the indolinone ring, or in the 3- or 4-position of the tetrahydroquinolinone ring, or in the 3-, 4- or 5-position of the tetrahydrobenzo[b]azepinone ring, and are obtained as racemates. These racemates can be separated into the optical isomers in a conventional manner.

The compounds of the formula I according to the invention have a powerful inhibitory action on a platelet aggregation and a powerful hypotensive action. They can accordingly be used as antihypertensives and for the prophylaxis and therapy of thrombo-embolic disorders.

The following methods have been used to investigate the pharmacodynamic properties of the products according to the invention:

1. Inhibition of platelet aggregation induced by collagen in rats.

The substances were administered orally to groups of 10-15 male Sprague-Dawley rats weighing from 200 to 250 g. 1 hour after the administration, blood was withdrawn under ether anesthetic and platelet-rich plasma was obtained by centrifugation (300 g for 10 minutes at 4° C.). The platelet aggregation was measured photometrically in a Born aggregometer Mark 3 with addition of $MgCl_2$ (end concentration of 10 mmoles/l) and of Collagen Stago (end concentration of 0.02 mg/ml). The maximim change in extinction per second was used as a measure of the aggregation.

The dose which inhibited collagen-induced platelet aggregation by 33% was determined as the ED 33%.

2. Antihypertensive action on spontaneously hypertonic rats (SHR)

The substances were administered orally to groups of 4-8 male spontaneously hypertonic Okamoto rats weighing from 270 to 360 g. The systolic blood pressure was measured non-operatively on the tail with the aid of piezo crystal recorders before and 2 hours after administration.

The dose which reduced the systolic pressure by 20% in comparison with the untreated control animals was determined, as the ED 20%.

3. Acute toxicity in mice

To determine the acute toxicity, the substances were administered intraperitoneally to groups of 5-10 female NMRI mice weighing from 20 to 23 g, and the mortality rate was determined.

The compounds according to the invention are of low toxicity and are powerful platelet aggregation inhibitors (Examples C, E, F and H) and antihypotensive agents (Examples F and H) (Table 1). The high specificity of the platelet aggregation-inhibiting action in comparison with that of the known reference substances I (6-(p-propoxyphenyl)-4,5-dihydro-3(2H)-pyridazinone from German Laid Open Application DOS No. 2,207,517) and II (6,6-(5-methyl-3-oxo-2,3,4,5-tetrahydropyridazin-6-yl)-1,2,3,4-tetrahydroquinolin-2-one from German Laid-Open Application DOS No. 2,845,220), which can be quantified by the difference between the aggregation-inhibiting dose and the antihypertensive dose (Q, see Table 1) and which favors use of the compounds according to the invention as pharmacotherapeutics, is unexpected and deserves particular mention.

TABLE 1

| Example | Inhibition of platelet aggregation ED 33% (1) | Antihypertensive action ED 20% (1) | Q (2) | Mortality rate x/n (3) |
|---|---|---|---|---|
| F | 0.18 | 2.2 | >12 | 1/5 |
| C | 1.3 | 10 | >7.7 | 3/5 |
| E | 0.87 | 10 | >11 | 0/5 |
| H | 0.33 | 4.0 | 12 | 0/5 |
| I | 0.63 | 1.2 | 1.9 | 10/10 |
| II | 0.23 | 0.79 | 3.4 | 2/5 |

(1) Rats, perorally, mg/kg
(2) ED 20%/ED 33%
(3) Mice, intraperitoneally, 1,000 mg/kg Accordingly, the present invention also relates to drugs containing a compound of the formula I.

The compounds according to the invention may be administered orally or parenterally (intravenously, intramuscularly or intraperitoneally) in a conventional manner.

The dosage depends on the age, condition and weight of the patient and on the route of administration. As a rule, the daily dose of active compound is from about 1 to 100 mg/kg of body weight in the case of oral administration, and from about 0.1 to 10 mg/kg of body weight in the case of parenteral administration. Under normal conditions, satisfactory results are achieved with daily oral doses of from 5 to 50 mg/kg or daily parenteral doses of from 0.5 to 5 mg/kg.

The novel compounds may be employed in the conventional solid or liquid pharmaceutical forms, eg. tablets, film tablets, capsules, powders, granules, coated tablets and suppositories. These are prepared in a conventional manner, the active compounds being mixed with the conventional pharmaceutical auxiliaries, such as tablet binders, fillers, preservatives, tablet disintegrants, flow regulators, softeners, wetting agents, dispersants, emulsifiers, solvents, retardants, antioxidants and/or propellants (cf. H. Sucker/Pharmazeutische Technologie, Thieme-Verlag, Stuttgart, 1978). The resulting formulations usually contain from 1 to 99 percent by weight of the active compound.

Preparation of the starting compounds (a) 20 ml (0.26 mole) of dimethylformamide are added dropwise, while stirring, to 120 g (0.9 mole) of anhydrous aluminum chloride in the course of a few minutes, whereupon a highly exothermic reaction starts. A mixture of 11.8 g (0.089 mole) of indolin-2-one and 11.3 g (0.09 mole) of cyclobutanedicarboxylic acid anhydride is then added a little at a time at 140° C., and stirring is continued at 140° C. and for 10 minutes. The melt is now poured onto 0.5 kg of ice, the solid precipitate is filtered off with suction and the aqueous phase is extracted several times with ethyl acetate to give 21.7 g (93.6%) of cis-2-(indolin-2-on-5-oyl)cyclobutanecarboxylic acid of melting point 211°-212° C.

The following compounds are obtained in a similar manner:

(b) cis-2-(1-Methyl-indolin-2-on-5-oyl)cyclobutanecarboxylic acid of melting point 210°-212° C., in a yield of 84%.

(c) cis-2-(Indolin-2-on-5-oyl)cyclopropanecarboxylic acid of melting point of 187°-190° C., in a yield of 81%.

(d) cis-2-(1-Methylindolin-2-on-5-oyl)cyclopropanecarboxylic acid of melting point 237°-240° C., in a yield of 81.5%.

(e) cis-2-(1,2,3,4-Tetrahydroquinolin-2-on-6-oyl)cyclobutanecarboxylic acid of melting point 155°-158° C., in a yield of 75%.

(f) cis-2-(1,2,3,4-Tetrahydroquinolin-2-on-6-oyl)cyclopropanecarboxylic acid of melting point 190°-194° C., in a yield of 57%.

(g) cis-2-(2,3,4,5-Tetrahydro-benzo[b]azepin-2-(1H)-on-7-oyl)cyclopropanecarboxylic acid, as a light yellow oil, in a yield of 70%.

Analysis for $C_{15}H_{15}NO_4$ (273): calculated: C 65.9, H 5.5, N 5.1. found: C 65.6, H 5.4, N 4.9.

EXAMPLE 1

(A) 5.22 g (0.02 mole) of cis-2-(indolin-2-on-5-oyl)cyclobutanecarboxylic acid are refluxed with 1.1 g (0.022 mole) of hydrazine hydrate and 50 ml of ethanol for 11 hours. The solid is filtered off with suction at room temperature and recrystallized from dimethylformamide/water to give 4.7 g (92%) of 2-(indolin-2-on-5-yl)-3,4-diazabicyclo[4.2.0]oct-2-en-5-one of melting point 309°-312° C.

Analysis for $C_{14}H_{13}N_3O_2$ (255): calculated: C 65.8, H 5.1, N 16.5. found: C 65.6, H 5.3, N 16.5.

The following compounds are obtained in a similar manner:

(B) 2-(1-Methylindolin-2-on-5-yl)-3,4-diazabicyclo[4.2.0]oct-2-en-5-one of melting point 256°-259° C., in a yield of 85%.

Analysis for $C_{15}H_{15}N_3O_2$ (269): calculated: C 66.9, H 5.6, N 15.6. found: C 66.6, H 5.7, N 15.5.

(C) 2-(Indolin-2-on-5-yl)-3,4-diazabicyclo[4.1.0]hept-2-en-5-one of melting point 305°-307° C., in a yield of 81%.

Analysis for $C_{13}H_{11}N_3O_2$ (241): calculated: C 64.7, H 4.6, N 17.4. found: C 64.7, H 4.6, N 17.5.

(D) 2-(1-Methylindolin-2-on-5-yl)-3,4-diazabicyclo[4.1.0]hept-2-en-5-one of melting point 265°-267° C., in a yield of 51%.

Analysis for $C_{14}H_{13}N_3O_2$ (255): calculated: C 65.9, H 5.1, N 16.5. found: C 65.4, H 5.1, N 17.0.

(E) 2-(1,2,3,4-Tetrahydroquinolin-2-on-6-yl)-3,4-diazabicyclo[4.2.0]oct-2-en-5-one of melting point 349°-353° C., in a yield of 84%.

Analysis for $C_{15}H_{15}N_3O_2$ (269): calculated: C 66.9, H 5.6, N 15.6. found: C 66.7, H 5.6, N 15.5.

(F) 2-(1,2,3,4-Tetrahydroquinolin-2-on-6-yl)-3,4-diazabicyclo[4.1.0]hept-2-en-5-one of melting point 310°-311° C. (decomposition), in a yield of 75%.

Analysis for $C_{14}H_{13}N_3O_2 \times 1/4 H_2O$: calculated: C 64.8, H 5.2, N 16.4. found: C 64.7, H 5.2, N 16.2.

(G) 2-(1,2,3,4-Tetrahydroquinolin-2-on-6-yl)-4-methyl-3,4-diazabicyclo[4.1.0]hept-2-en-5-one of melting point 255°-259° C., in a yield of 76%.

Analysis for $C_{15}H_{15}N_3O_2$ (269): calculated: C 66.9, H 5.6, N 15.6. found: C 66.6, H 5.7, N 15.5.

(H) 2-(2,3,4,5-Tetrahydro-benzo[b]azepin-2-(1H)-on-7-yl)-3,4-diazabicyclo[4.1.0]hept-2-en-5-one of melting point 308°-310° C., in a yield of 75%.

Analysis for $C_{15}H_{15}N_3O_2$ (269): calculated: C 66.9, H 5.6, N 15.6. found: C 66.2, H 5.3, N 15.4.

FORMULATION EXAMPLES

I. Tablets having the following composition are prepared:

| | |
|---|---|
| Active compound | 10 mg |
| Polyvinylpyrrolidone (mean molecular weight 25,000) | 170 mg |
| Polyethylene glycol (mean molecular weight 4,000) | 14 mg |
| Hydroxypropylmethylcellulose | 40 mg |
| Talc | 4 mg |
| Magnesium stearate | 2 mg |
| | 240 mg |

The active compound is moistened with a 10% strength aqueous solution of polyvinylpyrrolidone and forced through a sieve of 1.0 mm clear mesh width, and the granules are dried at 50° C. They are then mixed with polyethylene glycol (mean molecular weight 4,000), hydroxypropylmethylcellulose, talc and magnesium stearate, and the mixture is pressed to give tablets weighing 240 mg.

II. Coated tablets having the following composition are prepared:

| | |
|---|---|
| Active compound | 10 mg |
| Lactose | 90 mg |
| Corn starch | 60 mg |
| Polyvinylpyrrolidone | 6 mg |
| Magnesium stearate | 1 mg |
| | 167 mg |

The active compound, lactose and corn starch are mixed, moistened with an 8% strength aqueous solution of the polyvinylpyrrolidone, are granulated by passing through a 1.5 mm mesh sieve. The granules are dried at 50° C. and forced through a 1.0 mm sieve. The material thus obtained is mixed with magnesium stearate and the mixture is pressed to form tablet cores. These are coated in a conventional manner with a shell consisting substantially of sugar and talc.

We claim:

1. A 2-aryl-3,4-diazabicyclo[4.n.0]alk-2-en-5-one of the formula I

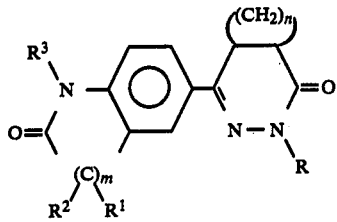

where m and n are identical or different and each is 1, 2 or 3 and R, $R^1$, $R^2$ and $R^3$ are identical or different and each is hydrogen or non-hindered alkyl of 1 to 6 C atoms.

2. 2-(Indolin-2-on-5-yl)-3,4-diazabicyclo[4.1.0]hept-2-en-5-one.

3. 2-(1,2,3,4-Tetrahydroquinolin-2-on-6-yl)-3,4-diazabicyclo[4.2.0]oct-2-en-5-one.

4. 2-(1,2,3,4-Tetrahydroquinolin-2-on-6yl)-3,4-diazabicyclo[4.1.0]hept-2en-5-one.

5. 2-(2,3,4,5-Tetrahydro-benzo[b]azepin-2-(1H)-on-7-yl)-3,4-diazabicyclo[4.1.0]hept-2-en-5-one.

6. A compound of the formula I as defined in claim 1 wherein R, $R^1$, $R^2$ and $R^3$ are each hydrogen.

7. A compound of the formula I as defined as in claim 1 wherein m is 1.

8. A compound of the formula I as defined in claim 6 wherein m is 1.

9. A pharmaceutical composition for treating thrombo-embolic disorders which comprises: a pharmaceutically acceptable auxiliary and an effective amount of a compound of the formula I of claim 1 as the active agent.

10. A pharmaceutical composition for treating thrombo-embolic disorders which comprises: a pharmaceutically acceptable auxiliary and an effective amount of a compound of the formula I of claim 6 as the active agent.

11. A pharmaceutical composition for treating thrombo-embolic disorders which comprises: a pharmaceutically acceptable auxiliary and an effective amount of a compound of the formula I of claim 2 as the active agent.

12. A pharmaceutical composition for treating thrombo-embolic disorders which comprises: a pharmaceutically acceptable auxiliary and an effective amount of a compound of the formula I of claim 11 as the active agent.

13. A method of treating thrombo-embolic disorders which comprises: administering orally or parenterally a composition as defined in claim 10, the daily oral dose being from 5 to 50 mg/kg of active agent and the daily parenteral dose being from 0.5 to 5 mg/kg of active agent.

14. A method of treating thrombo-embolic disorders which comprises: administering orally or parenterally a composition as defined in claim 13, the daily oral dose being from 5 to 50 mg/kg of active agent and the daily parenteral dose being from 0.5 to 5 mg/kg of active agent.

* * * * *